(12) United States Patent
Kanitz et al.

(10) Patent No.: US 6,258,469 B1
(45) Date of Patent: Jul. 10, 2001

(54) BENZIDINE DERIVATIVES AND THEIR PREPARATION AND USE

(75) Inventors: Andreas Kanitz, Höchstadt; Jörg Schumann, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/375,965

(22) Filed: Aug. 17, 1999

(30) Foreign Application Priority Data

Aug. 17, 1998 (DE) ................................. 198 37 198

(51) Int. Cl.[7] ........................ H05B 33/12; C07D 221/20; C07D 513/02
(52) U.S. Cl. .................... 428/690; 428/917; 428/704; 313/504; 313/506; 546/18
(58) Field of Search ..................... 428/690, 917, 428/704; 313/504, 506; 546/18; 548/125

(56) References Cited

U.S. PATENT DOCUMENTS 4,539,507   9/1985   VanSlyke et al. .................. 313/504

FOREIGN PATENT DOCUMENTS 227 434 A1   9/1985   (DD).
0 463 996 A2   1/1992   (EP).

OTHER PUBLICATIONS

S. Heun: "A comparative study of hole transport in vapor–deposited molecular glasses of N,N', N", N'"–tetrakis(4–methylphenyl)–(1,1'–biphenyl)–4,4'–diamine and N,N'–diphenyl–N,N'–bis(3–methylphenyl)–(1, 1'–biphenyl)–4–4'–diamine" in Chemical Physics 200 (1995) pp. 245–255; No month.

Jürgen Simmerer: "Ladungstransport in kolumnaren Phasen", doctoral thesis, University of Bayreuth, 1996 pp. 4–10, charge transport in columnar phases. No month.

Huoy–Jen Yuh et al.: "Charge Transport Processes in Molecularly Doped Polymers: Interaction effect between charge transporting molecules and polymers", in Mol. Cryst. Liq. Cryst., 1990, vol. 183, pp. 217–226; No month.

Yasuhiko Shirota et al.: "Multilayered organic electroluminescent device using a novel starburst molecule, 4,4', 4"–tris(3–methylphenylphenylamino)triphenylamine, as a hole transport material", in Appl. Phys. Lett. 65 (7), Aug. 15, 1994, pp. 807–809.

*Primary Examiner*—Marie Yamnitzky
*Assistant Examiner*—Ling Xu
(74) *Attorney, Agent, or Firm*—Herbert L. Lerner; Laurence A. Greenberg; Werner H. Stemer

(57) ABSTRACT

The benzidine derivatives of the invention are symmetrical compounds of the following structure:

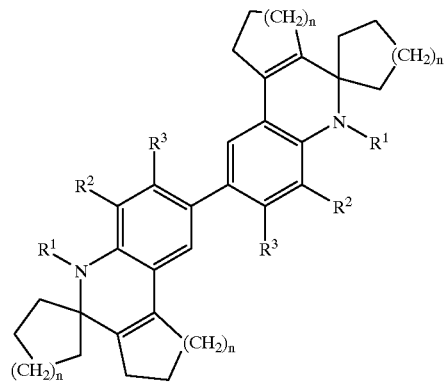

in which:

n=1, 2 or 3;
$R^1$=H, phenyl or 1-naphthyl,
$R^2$ and $R^3$ together form a fused benzene ring, an a- or b-fused naphthalene ring or a fused 1,2,5-thiadiazole ring.

13 Claims, No Drawings

BENZIDINE DERIVATIVES AND THEIR PREPARATION AND USE

BACKGROUND OF THE INVENTION

Field of the Invention

The invention relates to novel benzidine derivatives (benzidine=4,4'-diaminobiphenyl), to a process for their preparation, and to their use as hole transport materials in organic light emitting diodes (OLEDs).

Hole-transport materials based on tetraarylbenzidine are described, for example, in the dissertation by J. Simmerer "Ladungstransport in kolumnaren Phasen" [Charge transport in columnar phases], Bayreuth 1996, (pages 4 to 10); in this connection, see also: "Molecular Crystals and Liquid Crystals", Vol. 183 (1990), pages 217 to 226, "Applied Physics Letters", Vol. 65 (1994), pages 807 to 809, and "Chemical Physics", Vol. 200 (1995), pages 245 to 255.

The materials disclosed hitherto absorb and emit exclusively in the UV region of the electromagnetic spectrum.

SUMMARY OF THE INVENTION

It is therefore an object of the invention to provide novel benzidine derivatives, and a process for their preparation, that overcome the above-mentioned disadvantages of the prior art materials of this type and in particular emit in various regions of the visible spectral region and exhibit improved material properties such as higher glass transition temperatures than prior art materials.

It is a further object of the invention to provide improved organic light emitting diodes i.e. OLEDs incorporating benzidine derivatives of the invention as hole transport materials.

With the foregoing and other objects in view there are provided, in accordance with the invention, novel benzidine derivatives which are symmetrical fused and bridged spiro compounds.

The compounds of the invention are fluorescent chromophores. As a consequence of the limited twisting potential of the nitrogen and the fused ring structure, they are easier to oxidize than the benzidine derivatives disclosed hitherto, and hence they are highly suitable as hole-transport materials in organic light emitting diodes.

Owing to the presence of fused structural elements, further the longest-wavelength absorption of the compounds (1) is shifted into the visible spectral region. These compounds can thus—depending on the type of fusing—emit in various regions of the visible spectral region, enabling them to act simultaneously as emitter chromophore.

In accordance with a further feature of this invention, there are provided organic light emitting diodes (OLEDs) in which the novel fluorescent chromophore compounds of the invention serve as hole transport material, as well as pixel displays produced therewith for information monitors and light sources. An OLED in accordance with this invention comprises a layered construction including a transparent electrode, an organic chromophoric luminescent agent, an organic electron transport material, a metal electrode and a novel benzidine compound according to this invention. In such layered constructions the organic hole transport material, the chromophoric luminescent agent and the organic electron transport material can be combined into a single layer or in separate layers as desired. U.S. Pat. No. 4,539,507 can be consulted for various electron transport materials.

Compared with the materials used hitherto (based on tetraarylbenzidine), the benzidine derivatives of the invention exhibit improved material properties. These are, in particular, a higher glass transition temperature, which results in higher thermal stability of the light diodes, and a lower potential difference between the material and the ITO electrode (ITO=indium-tin oxide), which results in a higher light efficiency of the light diodes. This is because the HOMO potentials in the materials employed hitherto are lower in energetic terms than the potential of the ITO electrode, which produces a lower light efficiency.

The benzidine derivatives of the invention are symmetrical fused, and bridged spiro compounds of the following structure:

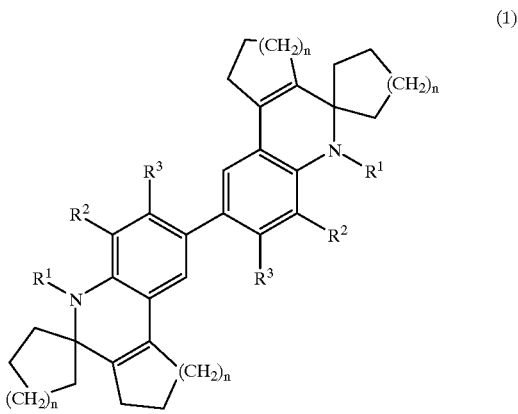

(1)

in which:
n=1, 2 or 3;
$R^1$=H, phenyl or 1-naphthyl,
$R^2$ and $R^3$ together form a fused benzene ring, an a- or b-fused naphthalene ring or a fused 1,2,5-thiadiazole ring.
Preferably n=2, $R^1$=H or phenyl, and $R^2$ and $R^3$ together form a fused benzene ring.

The novel benzidine derivatives are both fused, i.e. condensed, ring systems and bridged spiro compounds, i.e. compounds in which one carbon atom, the so-called spiro atom, is common to two rings. In addition, the amino groups in these benzidine derivatives are bridged, i.e. they resist being twisted, giving a very strong donor system. The assignment of $R^1$ in these benzidine derivatives is the same in each of the two rings to which $R^1$ is linked, and the fused ring formed by $R^2$ and $R^3$ together is the same in each of the two rings to which $R^2$ and $R^3$ are fused.

The benzidine derivatives (1) can be prepared in high purity in a simple manner from readily accessible starting materials, by condensing an amino-substituted aromatic or heteroaromatic compound, i.e. a heterocyclic compound, of structure (2) and a cycloaliphatic ketone of structure (3). The reactants are brought together, preferably in an equimolar ratio, without addition of a solvent, in the presence of a catalyst, in particular a catalytic amount of iodine, at elevated temperature, to give a bridged heterocyclic compound, i.e. an aromatic amine, of structure (4); the reaction of the two starting materials is preferably carried out at a temperature of from 200 to 250° C.

The resulting highly nucleophilic condensation product (4) is then oxidized to the benzidine derivative (1), preferably using hydrogen peroxide in a polar solvent, such as dimethylformamide. The oxidation can also be carried out using oxygen and other oxidants. It is advantageous to add a copper salt, such as copper (I) chloride (CuCl) in the oxidation using hydrogen peroxide.

The benzidine derivative (1) is also obtained when the condensation product (4) is isolated after its formation by distillation in a high vacuum, since under these conditions (4) is oxidized to the benzidine derivative owing to its high nucleophilicity. The honey-like product produced in the distillation contains a mixture of (1) and (4), which can easily be separated using diethyl ether. The benzidine derivative (1) is obtained as a flake-like precipitate, while the condensation product (4) remains in solution.

Compounds (1) in which $R^1$=H, phenyl or 1-naphthyl can be prepared as described. However, the phenyl and naphthyl compounds can also be prepared by arylating the corresponding H compound. The arylation is carried out in a manner known per se by a reaction analogous to the Ullmann reaction or the Heck reaction, for example by reaction with bromobenzene in the presence of a palladium catalyst.

Owing to their spiro structure the compounds of structure (1) are difficult to crystallize; they are produced in the form of amorphous powders and have a glass transition temperature of >220° C.

Other features which are considered as characteristic for the invention are set forth in the appended claims.

Although the invention is illustrated and described herein as embodied in benzidine derivatives, and their preparation and use, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

The invention will be explained in greater detail below with reference to working examples.

DESCRIPTION OF THE PREFERRED EMBODIMENTS

EXAMPLE 1

0.5 mol of 1-naphthylamine and about 1.5 g of iodine are heated to 200° C. in a 0.5 l three-neck flask fitted with reflux condenser, distillation apparatus and dropping funnel (with a tube extending down to the bottom of the flask); then 1.5 mol of cyclohexanone are added dropwise. The water formed during the reaction is distilled from the reaction flask. As soon as the water has been distilled off, the mixture is rectified in a fine vacuum (b.p. at $6 \times 10^{-5}$ mmHg: 150 to 180° C.). The oily product obtained is digested with diethyl ether, during which the benzidine derivative precipitates as yellowish flakes, which are separated by suction filtration.

EXAMPLE 2

The procedure initially corresponds to Example z1. After the water has been removed, the mixture is allowed to cool to 120° C., and 200 ml of dimethylformamide (as solubilizer) and 0.1 g of copper (I) chloride are then added to the reaction mixture. 60 g of 30% hydrogen peroxide are subsequently added dropwise through the reflux condenser. When the reaction is complete, the water formed during the reaction and the dimethylformamide are removed by distillation, and the mixture is then rectified in a high vacuum (b.p. at $\times 10^{-5}$ mmHg: 150 to 180° C.). The oily product obtained is digested with diethyl ether, during which the benzidine derivative precipitates as yellowish flakes, which are separated by suction filtration. The resulting product can also be sublimed for further purification.

EXAMPLE 3

0.5 mol of N-phenyl-l-naphthylamine and about 1.5 g of iodine are heated to 200° C. in a 0.5 l three-neck flask fitted with reflux condenser, distillation apparatus and dropping funnel (with a tube extending to the bottom of the flask); 1.5 mol of cyclohexanone are then added dropwise. The water formed during the reaction is distilled from the reaction flask. The procedure in Example 2 is then followed; the boiling point during the rectification in a high vacuum ($6 \times 10^{-5}$ mmHg) being from 220 to 240° C.

EXAMPLE 4

0.05 mol of the compound obtained as described in Example 1 or 2 and 0.05 mol of bromobenzene are dissolved in anhydrous toluene sparged with inert gas, and 3 mol-% of a palladium catalyst prepared from tri-o-tolylphosphine and palladium (II) acetate are added. 0.06 mol of sodium tert-butoxide is subsequently added to the reaction solution, which is refluxed for 15 hours. The resulting product is isolated by thin-layer chromatography and then sublimed. The same compound is obtained as in Example 3.

We claim:

1. A benzidine derivative of the structure

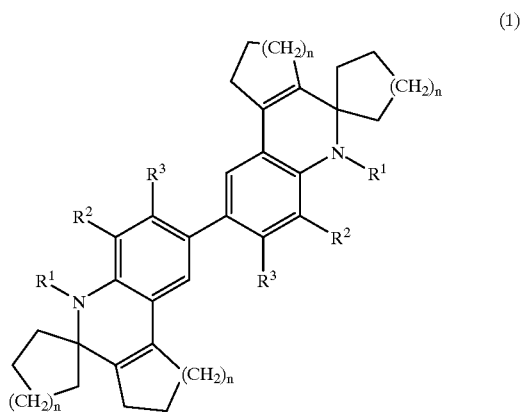

(1)

in which:
   n=1, 2 or 3;
   $R^1$=H, phenyl or 1-naphthyl, and
   $R^2$ and $R^3$ together form a fused benzene ring, an a- or b-fused naphthalene ring or a fused 1,2,5-thiadiazole ring.

2. A benzidine derivative as claimed in claim 1, in which n=2, $R^1$=H or phenyl, and $R^2$ and $R^3$ together form a fused benzene ring.

3. A benzidine derivative as claimed in claim 1 emitting in the visible spectral region.

4. A benzidine derivative as claimed in claim 1 having a glass transition temperature of at least 220° C.

5. A process for the preparation of a benzidine derivative as claimed in claim 1, comprising the steps of reacting a compound of the structure

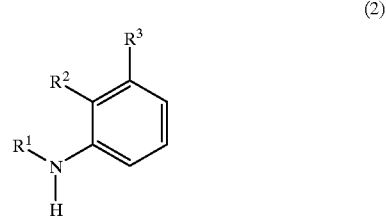

(2)

with a compound of the structure

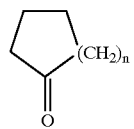
(3)

at an elevated temperature in the presence of a catalyst, to give a compound of the structure

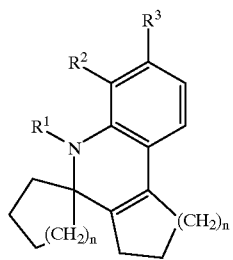
(4)

and converting the compound (4) into a benzidine derivative (1) by oxidation.

6. A process as claimed in claim 5 comprising an additional step of arylating a compound of formula (1) in which $R^1$=H to give a compound of formula (1) in which $R^1$=phenyl or naphthyl.

7. A process as claimed in claim 5, in which the catalyst is iodine.

8. A process as claimed in claim 5, in which the reaction is carried out at a temperature of from 200 to 250° C.

9. A process as claimed in claim 5, in which the oxidation is carried out using hydrogen peroxide.

10. A process as claimed in claim 9, in which a copper salt is added as catalyst.

11. A process as claimed in claim 9, in which the oxidation is carried out in a polar solvent.

12. A process as claimed in claim 6, in which the arylation is carried out using bromobenzene in the presence of a palladium catalyst.

13. An organic light emitting diode comprising a substrate, a transparent electrode, an organic hole transport material, an organic chromophoric luminescent agent, an organic electron transport material and a metal electrode, in which the organic hole transport material comprises a benzidine derivative as claimed in claim 1.

* * * * *